(12) United States Patent
Heidelbaugh et al.

(10) Patent No.: US 8,013,169 B2
(45) Date of Patent: Sep. 6, 2011

(54) NAPHTHYLMETHYLIMIDIZOLES AS THERAPEUTIC AGENTS

(75) Inventors: Todd M. Heidelbaugh, Fountain Valley, CA (US); Phong X. Nguyen, Placentia, CA (US); Ken Chow, Newport Coast, CA (US); Michael E. Garst, Newport Beach, CA (US)

(73) Assignee: Allergan, Inc, Irvine, CA (US)

( * ) Notice: Subject to any disclaimer, the term of this patent is extended or adjusted under 35 U.S.C. 154(b) by 0 days.

(21) Appl. No.: 12/522,882

(22) PCT Filed: Jan. 4, 2008

(86) PCT No.: PCT/US2008/050161
§ 371 (c)(1), (2), (4) Date: Jul. 10, 2009

(87) PCT Pub. No.: WO2008/086131
PCT Pub. Date: Jul. 17, 2008

(65) Prior Publication Data
US 2010/0004305 A1    Jan. 7, 2010

Related U.S. Application Data

(60) Provisional application No. 60/884,713, filed on Jan. 12, 2007, provisional application No. 60/917,811, filed on May 14, 2007.

(51) Int. Cl.
*C07D 233/64* (2006.01)
(52) U.S. Cl. .................................................. 548/346.1
(58) Field of Classification Search ................ 548/346.1
See application file for complete search history.

(56) References Cited

U.S. PATENT DOCUMENTS

| | | | |
|---|---|---|---|
| 4,814,343 | A | 3/1989 | Cossement |
| 5,151,526 | A | 9/1992 | Hsu et al. |
| 6,329,369 | B1 | 12/2001 | Chow et al. |
| 6,465,486 | B1 | 10/2002 | Baxter |
| 6,841,684 | B2 | 1/2005 | Chow et al. |
| 2002/0019390 | A1 | 2/2002 | Wong et al. |
| 2003/0023098 | A1 | 1/2003 | Chow et al. |
| 2006/0069144 | A1* | 3/2006 | Heidelbaugh et al. ........ 514/389 |

FOREIGN PATENT DOCUMENTS

| | | |
|---|---|---|
| EP | 0 024 829 | 8/1980 |
| EP | 1 413 576 | 12/1998 |
| WO | WO 98/46572 | 10/1998 |
| WO | WO 99/28300 | 6/1999 |
| WO | WO 01/00586 | 1/2001 |
| WO | WO 02/076950 | 10/2002 |
| WO | WO 2006/036497 | 4/2006 |
| WO | WO 2006/036507 | 4/2006 |

OTHER PUBLICATIONS

Analog [online], [retrieved on Apr. 25, 2008]. Retrieved from the Internet, URL; http://medical-dictionary.thefreedictionary.com/p/analog.*
Prodrug [online], [retrieved on Mar. 11, 2007]. Retrieved from the Internet, URL; http:llen.wikipedia.orglwikilProdrug>.*
Stress incontinence [online], [retrieved on Aug. 26, 2010]. Retrieved from the internet, URL; http://www.nlm.nih.gov/medlineplus/ency/article/000891.htm.*
Glaucoma [online], [retrieved on Aug. 26, 2010]. Retrieved from the internet, URL; http://www.webmd.com/eye-health/glaucoma-eyes?page=3.*
Prezeslawski R., et al.; "Synthesis and Alpha2-Adrenergic Activity of Quinoline and Quinoxaline Analogues of Medetomidine"; Proceedings of the Erdec Scientific Conference on Defense Research; Nov. 1994; pp. 121-127; XP008091151.
Seoung-Soo Hong et al; "A Structure-Activity Relationship Study of Benzylic Modifications of 441-(I -Naphthyl)ethyl]-1H-imidazoleos n al- and az-Adrenergic Receptors"; J. Med. Chem. 1994,37, 2328-2333.
Yoshiya Amemiya et al. "Synthesis and a-Adrenergic Activities of 2- and 4-Substituted Imidazoline and Imidazole Analogues".
Shilpa G. Lalchandani, et al; "Medetomidine analogs as selective agonists for the human a2-adrenoceptors"; Biochemical Pharmacology 67 (2004) 87-96.
D.D Miller, et al.; "Synthesis and biological Activity of a Series of Comformationally Restricted Analogs of 4-Substituted Imidazoles as $a_2$-Adrenergic Agonists"; Proceedings of the Erdec Scientific Conference on Defense Research; Nov. 1994; pp. 113-119.
Yoshiya Amemiya et al.; "Medetomidine Analogs as $a_2$-Adrenergic Agonists"; Egypt J. Pharm. Sci. 35, No. 1-6, pp. 403-410; 1994.
Yoshiya Amemiya et al.; "Synthesis and a-AdrenergicActivvities of 2- and 4-Substituted Imidazoline and Imidazole Analogues of α and β-Naphthalene"; Egypt J. Pharm. Sci. 35, No. 1-6, pp. 91-112; 1994.
B. V. Venkataraman el at.; "Structure-Activity Studies of New Imidazolines on Adrenoceptors of Rat Aorta and Puman Platelets"; Naunyn-Schmiedeberg's Arch Pharma, 344:454-463; 1994.

* cited by examiner

*Primary Examiner* — Shawquia Young
(74) *Attorney, Agent, or Firm* — Doina G. Ene; John E. Wurst; Kevin J. Forrestal

(57) ABSTRACT

Disclosed herein is a compound of the formula (a): Therapeutic methods, compositions and medicaments related thereto are also disclosed.

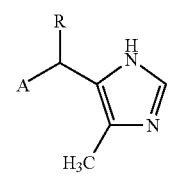

(a)

13 Claims, No Drawings

NAPHTHYLMETHYLIMIDIZOLES AS THERAPEUTIC AGENTS

CROSS REFERENCE TO RELATED APPLICATIONS

This is a national stage application under 35 U.S.C. §371 of PCT patent application PCT/US08/50161, filed on Jan. 4, 2008, which claims the benefit of U.S. Provisional Patent Application 60/884,713, filed Jan. 12, 2007 and U.S. Provisional Application Ser. No. 60/917,811, filed May 14, 2007, each of which is hereby incorporated by reference in its entirety.

DESCRIPTION OF THE INVENTION

Disclosed herein is a compound of the formula

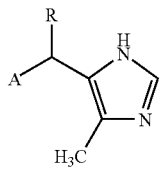

wherein R is H, $C_{1-4}$ alkyl, or $CF_3$;

A is naphthyl having 0, 1, 2, or 3 stable substituents consisting of from 1 to 8 heavy atoms and any required hydrogen atoms, said heavy atoms being selected from C, N, O, S, F, Cl, Br, I, and any combination thereof.

Another embodiment is a method comprising administering a compound disclosed herein to a patient in need thereof for the treatment of glaucoma or ocular hypertension.

DEFINITIONS, EXPLANATIONS, AND EXAMPLES

Unless explicitly and unambiguously indicated otherwise, the definitions, explanations, and examples provided in this section shall be used to determine the meaning of a particular term or expression where there is any ambiguity arising from other parts of this document or from any disclosure incorporated by reference herein.

Hydrocarbyl is a moiety consisting of carbon and hydrogen, including, but not limited to:
1. alkyl, which is hydrocarbyl containing no double or triple carbon-carbon bonds; alkyl includes, but is not limited to:
    linear alkyl, cyclic alkyl, branched alkyl, and combinations thereof;
    $C_{1-4}$ alkyl, which refers to alkyl having 1, 2, 3, or 4 carbon atoms, including, but no limited to, methyl, ethyl, isopropyl, cyclopropyl, n-propyl, n-butyl and the like;
    $C_{1-6}$ alkyl, which refers to alkyl having 1, 2, 3, 4, 5, or 6 carbon atoms; including, but not limited to methyl, ethyl, propyl isomers, cyclopropyl, butyl isomers, cyclobutyl, pentyl isomers, cyclopentyl, hexyl isomers, cyclohexyl, and the like;
    combinations of these terms are possible, and their meanings should be obvious to those of ordinary skill in the art; for example $C_{1-6}$ linear alkyl would refer to $C_{1-6}$ alkyl which is also linear;
2. alkenyl, which is hydrocarbyl containing one or more carbon-carbon double bonds; alkenyl includes, but is not limited to:
    linear alkenyl, cyclic alkenyl, branched alkenyl, and combinations thereof;
    alkenyl having 1, 2, 3, or more carbon-carbon double bonds;
3. alkynyl, which is hydrocarbyl containing one or more carbon-carbon triple bonds; alkynyl includes, but is not limited to:
    linear alkynyl, cyclic alkynyl, branched alkynyl, and combinations thereof;
    alkynyl having 1, 2, 3, or more carbon-carbon double bonds;
4. aryl, provided that it contains no heteroatoms either in a ring or as a substituent;
5. combinations of any of the above;
6. $C_{1-4}$ hydrocarbyl, which refers to hydrocarbyl having 1, 2, 3, or 4 carbon atoms; and
7. $C_{1-6}$ hydrocarbyl, which refers to hydrocarbyl having 1, 2, 3, 4, 5, or 6 carbon atoms.

Alkoxy is O-alkyl, such as $OCH_3$, O-ethyl, O-isopropyl, and the like.

Mercaptoalkyl is S-alkyl, such as $SCH_3$, S-ethyl, S-isopropyl, and the like

Acyloxy is

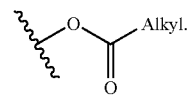

Acyl is

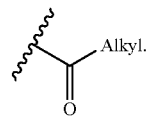

$C_{1-5}$ acyl is acyl having 1, 2, 3, 4, or 5 carbon atoms.

A compound, substituent, moiety, or any structural feature is stable if it is sufficiently stable for the compound to be isolated for at least 12 hours at room temperature under normal atmospheric conditions, or if it is sufficiently stable to be useful for at least one use disclosed herein.

A heavy atom is an atom which is not hydrogen.

A heteroatom is an atom which is not carbon or hydrogen.

A pharmaceutically acceptable salt is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid or another salt.

Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Unless otherwise indicated, reference to a compound should be construed broadly to include pharmaceutically acceptable salts, and tautomers of the depicted structure. For example, the structures herein are intended to include, but are not limited to, the tautomeric forms shown below.

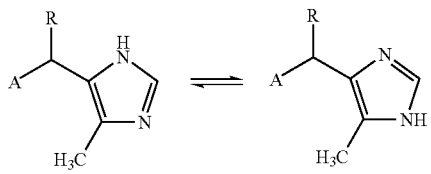

Unless stereochemistry is explicitly depicted, a structure is intended to include every possible stereoisomer, both pure or in any possible mixture.

For the purposes of this disclosure, "treat," "treating," or "treatment" refer to the use of a compound, composition, therapeutically active agent, or drug in the diagnosis, cure, mitigation, treatment, prevention of disease or other undesirable condition, or to affect the structure or any function of the body of man or other animals.

R is H, $C_{1-4}$ alkyl, or $CF_3$. Thus, the following compounds are contemplated.

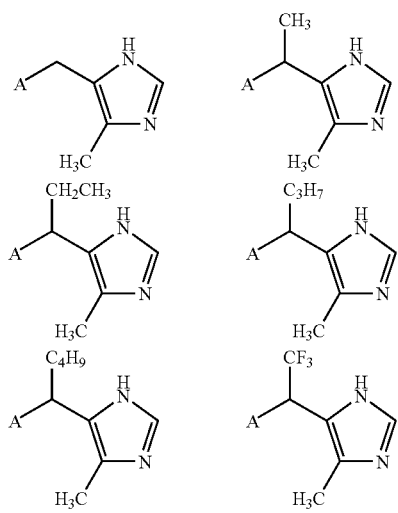

In one embodiment R is H.

A is quinolinyl having 0, 1, 2, or 3 stable substituents consisting of from 1 to 8 heavy atoms and any required hydrogen atoms, said heavy atoms being selected from C, N, O, S, F, Cl, Br, I, and any combination thereof.

Naphthyl is

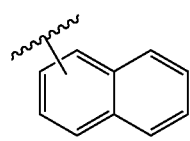

which may have substituents according to the parameters set forth herein.

Thus, for example, A may be any of the structures shown below or the like, wherein $R^1$, $R^2$, and $R^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

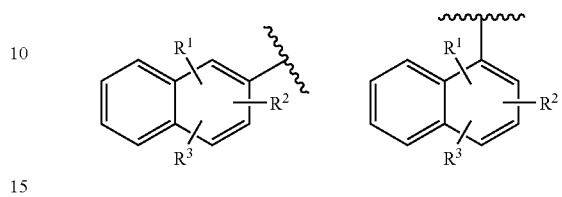

The position of $R^1$, $R^2$, and $R^3$ may be anywhere on the ring system, and are not limited to the particular ring where they are located in the structural depiction.

While not intending to be limiting, examples of stable substituents consisting of from 1 to 8 heavy atoms and any required hydrogen atoms include:

hydrocarbyl, including alkyl, such as methyl, ethyl, propyl isomers, butyl isomers, and the like;

alkenyl, alkynyl, and phenyl;

alkoxy, mercaptoalkyl, acyloxy, amino, including $NH_2$, NH-alkyl, $N(alkyl)_2$, where the alkyl groups are the same or different;

halo, including F, Cl, Br, and I; and $CH_2CN$; CN; $NO_2$; OH.

If a substituent is a salt, for example of a carboxylic acid or an amine, the counterion of said salt, i.e. the ion that is not covalently bonded to the remainder of the molecule is not counted for the purposes of the number of heavy atoms in a substituent. Thus, for example, the salt $—CO_2^-Na^+$ is a stable substituent consisting of 3 heavy atoms, i.e. sodium is not counted. In another example, the salt $—NH(Me)_2^+Cl^-$ is a stable substituent consisting of 3 heavy atoms, i.e. chlorine is not counted.

In one embodiment, the substituents selected from are methyl, ethyl, propyl isomers, F, Cl, Br, I, $OCH_3$, $NH_2$, $N(CH_3)_2$, and combinations thereof.

In another embodiment substituents are selected from $CH_3$, ethyl, t-butyl, ethenyl, ethynyl, $OCH_3$, NHMe, $NMe_2$, Br, Cl, F, phenyl, and combinations thereof.

In another embodiment A is unsubstituted.

Another embodiment is a compound having the formula

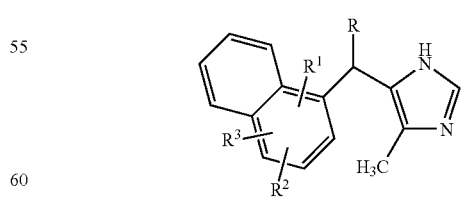

wherein $R^1$, $R^2$, and $R^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

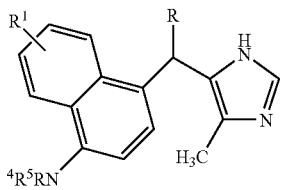

wherein $R^1$ is hydrogen or a stable substituent consisting of from 1 to 8 heavy atoms and any required hydrogen atoms, said heavy atoms being selected from C, N, O, S, F, Cl, Br, I, and any combination thereof; and n is 0, 1, 2, or 3;
$R^4$ and $R^5$ are independently H, $C_{1-4}$ alkyl, or $C_{1-5}$ acyl.

Another embodiment is a compound having the formula

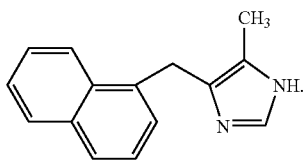

Another embodiment is a compound having the formula

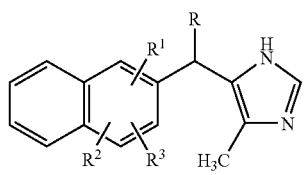

wherein $R^1$, $R^2$, and $R^3$ are independently hydrogen or stable substituents consisting of from 1 to 8 heavy atoms and any required hydrogen atoms, said heavy atoms being selected from C, N, O, S, F, Cl, Br, I, and any combination thereof; and n is 0, 1, 2, or 3.

Another embodiment is a compound having the formula

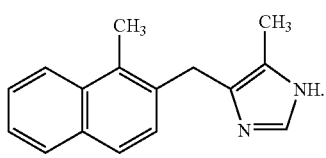

Another embodiment is a compound having the formula

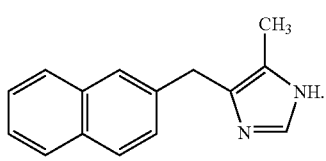

Biological Data

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as □-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×106 cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 µg), receptor (1-2 µg) and G protein (1-2 µg). 40 µg salmon sperm DNA may also be included in the transfection mixture. Fresh media is added on the following day and 1-2 days later, cells are harvested and frozen in 50 assay aliquots. Cells are thawed and 100 µl added to 100 µl aliquots of various concentrations of drugs in triplicate in 96-well dishes. Incubations continue 72-96 hr at 37° C. After washing with phosphate-buffered saline, β-galactosidase enzyme activity is determined by adding 200 µl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors. The EC$_{50}$ is the concentration at which the drug effect is half of its maximal effect.

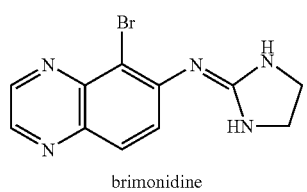

brimonidine

The results of the RSAT assay with several exemplary compounds of the invention are disclosed in Table 1 above together with the chemical formulas of these exemplary compounds. EC$_{50}$ values are nanomolar. NA stands for "not active" at concentrations less than 10 micromolar. IA stands for "intrinsic activity."

TABLE 1

| Structure | Alpha 1A EC50 (IA) | Alpha 2A EC50 (IA) | Alpha 2B EC50 (IA) | Alpha 2C EC50 (IA) |
| --- | --- | --- | --- | --- |
| 7 | 13 (1.2) | NA | NA | NA |
| 5 | 11.6 (1.26) | NA | 553 (0.31) | NA |
| 8 | 55 (1.01) | NA | 146 (0.46) | NA |

Compounds 7, 5, and 8 are named as follows:

N-methyl-4-((5-methyl-1H-imidazol-4-yl)methyl)naphthalen-1-amine (7);

N,N-dimethyl-4-((5-methyl-1H-imidazol-4-yl)methyl)naphthalen-1-amine (5); and 4-((5-methyl-1H-imidazol-4-yl)methyl)naphthalen-1-amine (8).

Compounds H4-H22 are hypothetical examples of compounds that are useful as disclosed herein.

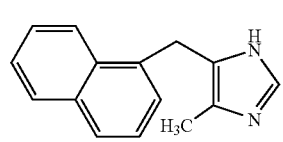

H5

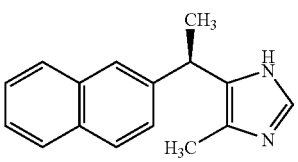

H6

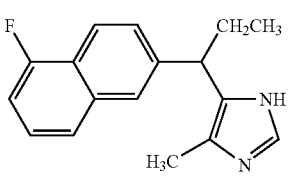

H7

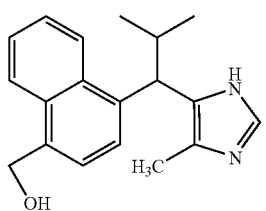

H8

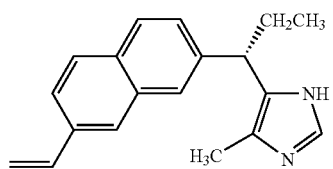

H9

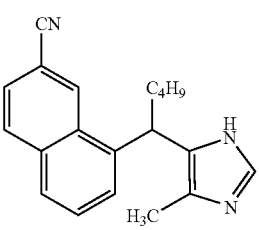

H10

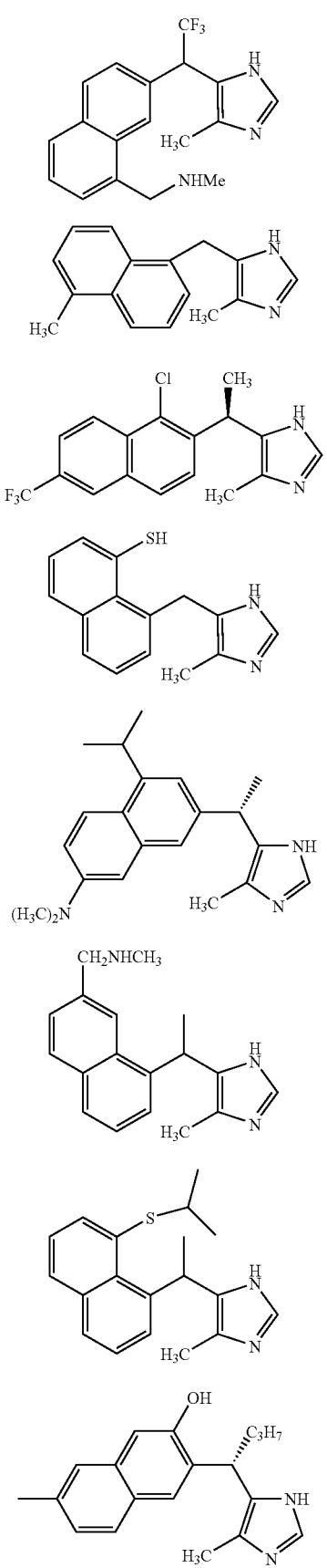
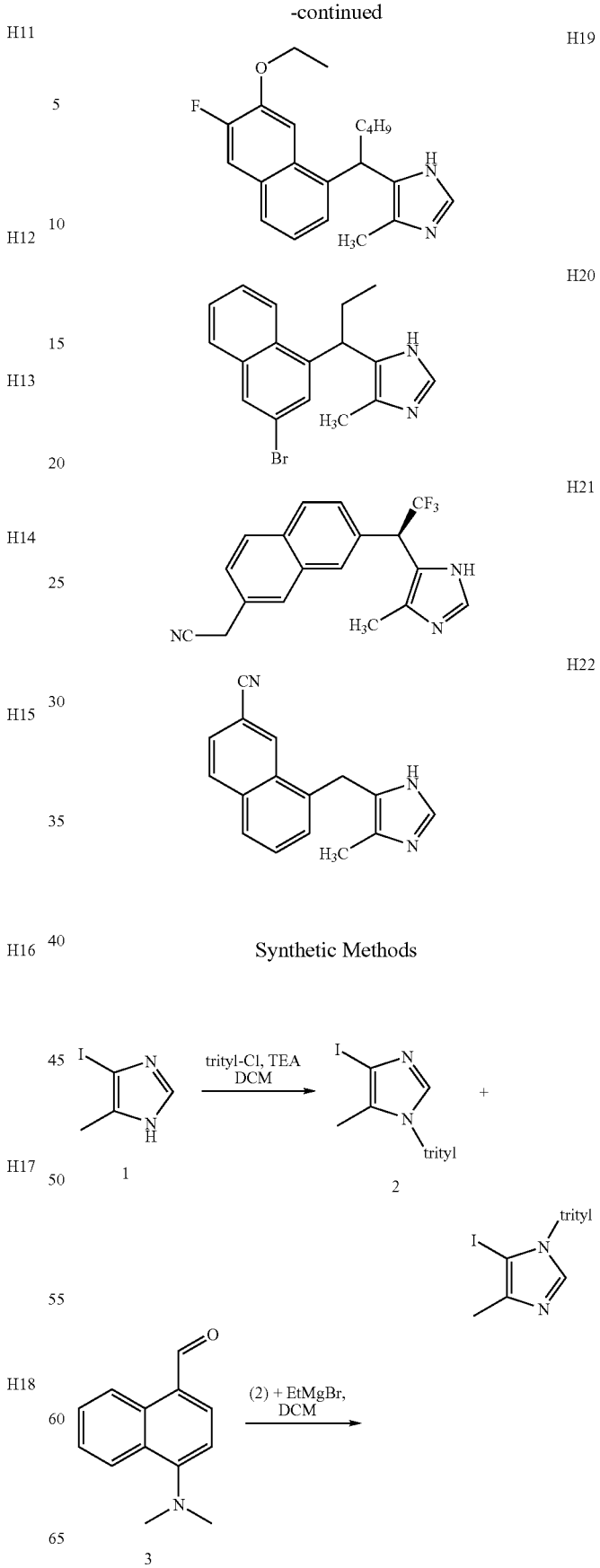
Synthetic Methods

-continued

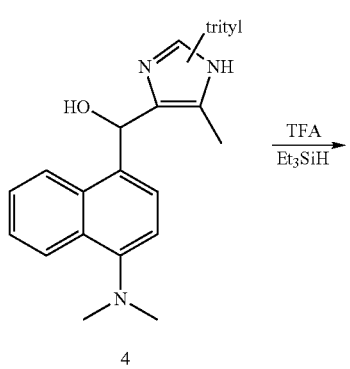

4

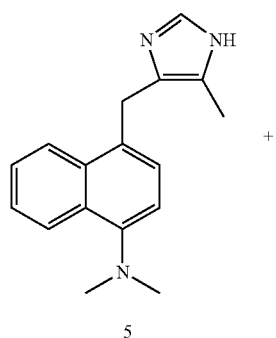

5

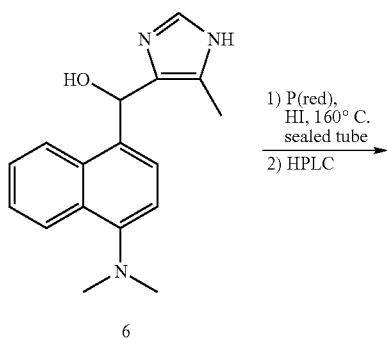

6

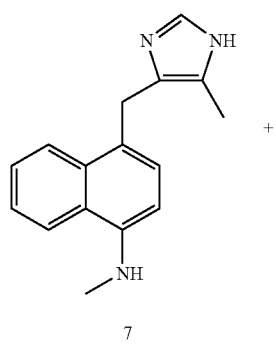

7

-continued

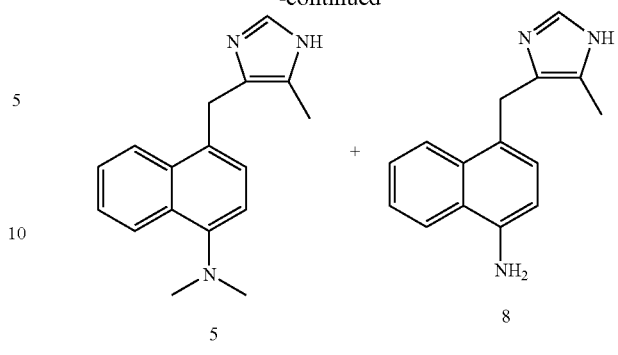

5                                           8

4-Iodo-5-methyl-1-trityl-1H-imidazole and 5 iodo-4-methyl-1-trityl-1H-imidazole (2): A mixture of 4-iodo-5-methyl-1H-imidazole (1) (10.5 g, 50.7 mmol) and trityl chloride (14.4 g, 50.7 mmol) in dichloromethane (100 mL) was added triethylamine (17.6 mL, 126 mmol), and the reaction mixture was stirred at room temperature overnight. The mixture was quenched with ammonium chloride (aq), and the aqueous medium was extracted twice with dichloromethane (400 mL). The pooled organic layers were dried over magnesium sulfate. The mixture was filtered and the solvents were removed under vacuum to give sticky yellow solid. The crude product was triturated in hexane to give a mixture of 4-iodo-5-methyl-1-trityl-1H-imidazole and 5 iodo-4-methyl-1-trityl-1H-imidazole (2) as a white solid (20 g, 44.4 mmol, 87% yield).

(4-Dimethylamino)naphthalen-1-yl)(5-methyl-1-trityl-1H-imidazol-4-yl)methanol and (4-(dimethylamino)naphthalen-1-yl)-4-methyl-1-trityl-1H-imidazol-5-yl)methanol (4): A solution of (2) (5.1 g, 11.3 mmol) in dichloromethane (70 ml) was added ethyl magnesium bromide (3.0 M in diethyl ether, 3.8 mL, 11.4 mmol) drop wise at rt. The mixture was stirred for 1 h and a solution of 4-(dimethylamino)-1-naphthaldehyde (3) (1.15 g, 7.35 mmol) in dichloromethane (30 mL) was added drop wise via addition funnel. The reaction mixture was stirred at room temperature (n) overnight. The reaction mixture was quenched with ammonium chloride (aq). The resulting aqueous layer was extracted twice with dichloromethane (300 mL). The pooled organic layers were dried over magnesium sulfate. The mixture was filtered, and the solvents were removed under vacuum. The residue was purified by chromatography on silica gel with 1 to 2% saturated ammonia methanol in dichloromethane to give a crude (4-(dimethylamino)naphthalen-1-yl)(5-methyl-1-trityl-1H-imidazol-4-yl)methanol and (4-(dimethylamino)naphthalen-1-yl)(4-methyl-1-trityl-1H-imidazol-5-yl)methanol (4) (3.35 g, 6.40 mmol, 87% yield).

N,N-Dimethyl-4-((5-methyl-1H-imidazol-4-yl)methyl)naphthalen-1-amine (5): A solution of (4) (3.35 g, 6.40 mmol) in TFA (30 mL) was added triethylsilane (6 mL, 38.4 mmol). The reaction mixture was stirred at room temperature overnight. TFA was removed under vacuum. The residue was basified with 2 M sodium hydroxide to pH>7. The aqueous layer was extracted three times with chloroform/isopropanol (3:1200 mL). The pooled organic layers were dried over magnesium sulfate. The mixture was filtered and the solvents were removed under vacuum. The residue was purified by chromatography on silica gel with 2 to 5% saturated ammonia methanol in dichloromethane to give N,N-dimethyl-4-((5-methyl-1H-imidazol-4-yl)methyl)naphthalen-1-amine (5) (0.55 g, 2.07 mmol, 32% yield), and (4-(dimethylamino)naphthalen-1-yl)(5-methyl-1H-imidazol-4-yl)methanol (6) (0.45 g, 1.60 mmol, 25% yield).

N,N-Dimethyl-4-((5-methyl-1H-imidazol-4-yl)methyl)naphthalen-1-amine (5) ¹H NMR (500 MHz, CDCl₃): δ 8.29-8.28 (m, 1H), 7.98-7.96 (m, 1H), 7.50-7.45 (m, 2H), 7.37 (s, 1H), 7.18 (d, J=7.5 Hz, 1H), 7.0 (d, J=8.0 Hz, 1H), 4.26 (s, 3H), 2.87 (s, 6H), 2.24 (s, 3H).

N-Methyl-4-((5-methyl-1H-imidazol-4-yl)methyl)naphthalen-1-amine (7) and 4-((5-methyl-1H-imidazol-4-yl)methyl)naphthalen-1-amine (8): A mixture of (6) (0.45 g, 1.60 mmol) and red phosphorus (0.50 g, 16.1 mmol) in hydroiodic acid (57% in water, 8 mL) was heated in sealed tube at 160° C. over night. The reaction mixture was cooled to rt, and the sealed tube was slowly open to release the gas built up inside. The content was poured into crushed ice, and carefully basified with NaOH (aq.) to pH>7. The aqueous layer was diluted with chloroform/isopropanol (3:1, 100 mL). The mixture was filtered through a bed of Celite to removed phosphorus. The layers were separated. The aqueous layer was extracted twice with chloroform/isopropanol (3:1, 100 ml). The pooled organic layers were dried over magnesium sulfate. The mixture was filtered and the solvents were removed under vacuum. The residue was purified by chromatography on silica gel with 3% ammonia saturated methanol in dichloromethane to give a mixture of (5), N-methyl-4-((5-methyl-1H-imidazol-4-yl)methyl)naphthalen-1-amine (7), and 4-((5-methyl-1H-imidazol-4-yl)methyl)naphthalen-1-amine (8) (0.296 g). The mixture (110 mg) was purified by reverse phase HPLC to separate (7) (52 mg), and (8) (17 mg).

(7) ¹H NMR (500 MHz, CDCl₃): δ 7.92-7.90 (m, 1H), 7.83-7.82 (m, 1H), 7.48-7.42 (m, 2H), 7.33 (s, 1H), 7.19 (d, J=7.50 Hz, 1H), 6.53 (d, J=7.50 Hz, 1H), 4.22 (s, 2H), 3.01 (s, 3H), 2.25 (s, 3H).

(8) ¹H NMR (500 MHz, CDCl₃): δ 7.91-7.84 (m, 1H), 7.47-7.45 (m, 2H), 7.30 (s, 1H), 7.06 (d, J=7.50 Hz, 1H), 6.69 (d, J=7.00, 1H), 4.20 (s, 2H), 2.22 (s, 3H).

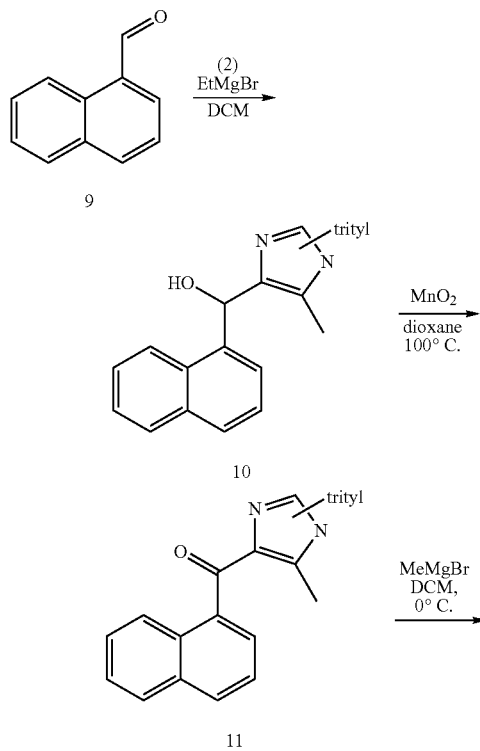

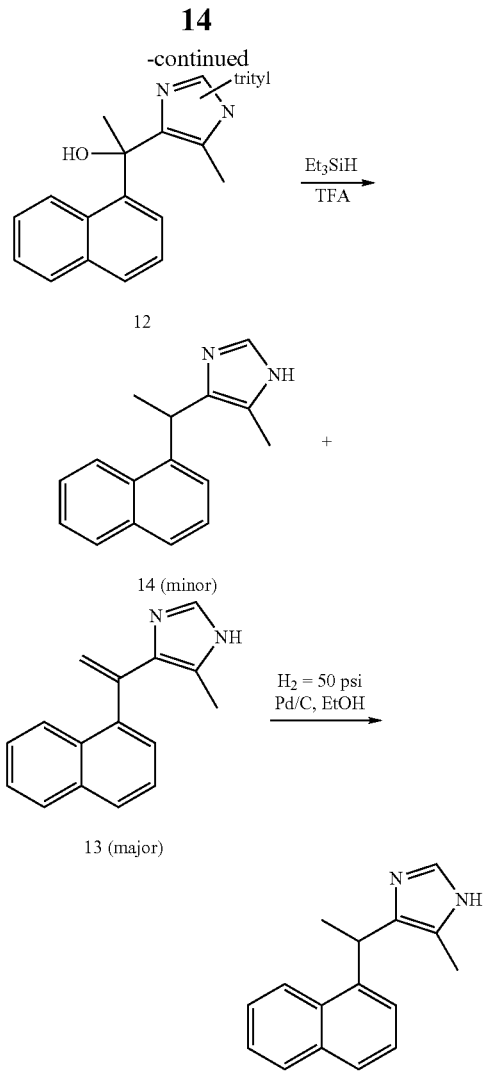

(5-methyl-1-trityl-1H-imidazol-4-yl)naphthalen-1-yl)methanol and (4-methyl-1-trityl-1H-imidazol-5-yl)(naphthalen-1-yl)methanol (10): The same synthetic route to make (4) was used.

(5-Methyl-1-trityl-1H-imidazol-4-yl)(naphthalen-1-yl)methanone and (4-methyl-1-trityl-1H-imidazol-5-yl)(naphthalen-1-yl)methanone (11): A mixture of (10) (4.48 g, 8.33 mmol) and manganese dioxide (9.85 g, 93.6 mmol) in dioxane (50 mL) was heated at 100° C. overnight. The mixture was cooled to rt, and filtered through a bed of Celite and bed was washed with ethyl acetate. The filtrate was concentrated under vacuum. The residue was purified by chromatography on silica gel with 80% hexane and 20% ethyl acetate to give (5-methyl-1-trityl-1H-imidazol-4-yl)(naphthalen-1-yl)methanone and (4-methyl-1-trityl-1H-imidazol-5-yl)(naphthalen-1-yl)methanone (11) (2.52 g, 5.27 mmol, 56% yield).

1-(5-Methyl-1-trityl-1H-imidazolyl)-1-(naphthalen-1-yl)ethanol and 1-(4-methyl-1-trityl-1H-imidazol-5-yl)-1-(naphthalen-1-yl)ethanol (12): A solution of (11) (1.33 g, 2.78 mmol) in dichloromethane (50 mL) at 0° C. was added methyl magnesium bromide (3.0 M in diethyl ether, 1.85 mL, 5.50 mmol) drop wise. The reaction mixture was warmed to room temperature over night. The mixture was quenched with ammonium chloride (aq). The resulting aqueous layer was extracted with chloroform three times (200 mL). The pooled organic layers were dried over magnesium sulfate. The mixture was filtered, and the solvents were removed under vacuum. The residue was purified by chromatography on silica gel with 50% hexane and 50% ethyl acetate to give 1-(5-methyl-1-trityl-1H-imidazol-4-yl)-1-(naphthalen-1-yl) ethanol and 1-(4-methyl-1-trityl-1H-imidazol-5-yl)-1-(naphthalen-1-yl)ethanol (12) (1.21 g, 2.45 mmol, 88% yield).

5-Methyl-4-(1-(naphthalen-1-yl)vinyl)-1H-imidazole (13): The same synthetic route to make (5) was used. The product mixture of 5-methyl-4-(1-(naphthalen-1-yl)vinyl)-1H-imidazole (13) (major) and 5-methyl-4-(1-(naphthalen-1-yl)ethyl)-1H-imidazole (14) (minor) was used in the next step.

5-Methyl-4-(1-(naphthalen-1-yl)ethyl)-1H-imidazole (14): Crude (13) in ethanol was hydrogenated (50 psi $H_2$) over Pd/C (10%, 0.19 g) over night. The reaction was filtered through a bed of Celite. The filtrate was added silica gel, and the solvent was removed under vacuum. Crude product on silica was purified by chromatography on silica gel with 2% saturated ammonia methanol in dichloromethane to give (14) as a light tan foam (423 mg, 1.79 mmol, 73% over 2 steps).

(14) $^1$H NMR (300 MHz, $CDCl_3$): δ 8.06-8.03 (m, 1H), 7.78-7.75 (m, 1H), 7.62 (d, J=8.10 Hz, 1H), 7.42-7.37 (m, 3H), 7.32 (q, J=7.8 Hz, 1H), 7.20 (s, 1H), 4.87 (q, J=7.2 Hz, 1H), 1.99 (s, 3H), 1.71 (d, J=7.2 Hz, 3H).

Alternate attachment of the naphthyl ring may be obtained by using 2-naphthaldehyde or a substituted 2-naphthaldehyde instead of 9.

Additional substitution on the naphthyl ring of A may be obtained by purchasing the corresponding substituted naphthaldehyde. Alternatively, additional substituents may be added to the naphthyl ring by methods known in the art.

Different R groups may be obtained by using the corresponding Grignard reagent instead of MeMgBr in the conversion of 11 to 12.

Other alternate routes to a wide variety of compounds are readily apparent to those skilled in the art.

These compounds will be useful for the treatment of mammals, including humans, with a range of conditions and diseases that include, but are not limited to, ischemic neuropathies, optic neuropathy, neuropathic pain, visceral pain, corneal pain, headache pain, migraine, cancer pain, back pain, irritable bowel syndrome pain, muscle pain and pain associated with diabetic neuropathy, the treatment of diabetic retinopathy, other retinal degenerative conditions, cognitive deficits, neuropsychiatric conditions, drug dependence and addiction, withdrawal symptoms, spasticity, autism, Huntington's disease, attention deficit disorder, attention deficit hyperactivity disorder ADHD, obsessive-compulsive disorders, Tourette's disorder, Parkinson's ALS, and other motor or movement disorders and diseases.

Other uses include dilation of the pupil, increase blood pressure, treating nasal congestion, and vasoconstriction in ocular tissue.

These compounds may be formulated into solid, liquid, or other types of dosage forms using methods known in the art. Both formulation of dosage forms and determination of a therapeutically effective dose can be readily made by a person of ordinary skill using routine methods.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the claims.

What is claimed is:

1. A compound of the formula:

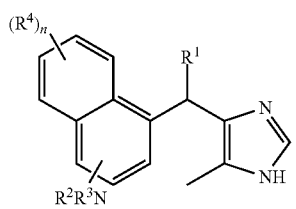

wherein $R^1$ is H, $C_{1-4}$ alkyl, or $CF_3$; and,
$R^2$ and $R^3$ are independently H, $C_{1-4}$ alkyl, $C_{1-5}$ acyl, cyano, alkylsulfonamide or arylsulfonamide,
$R^4$ is hydrogen or a stable substituent consisting of from 1 to 8 heavy atoms and any required hydrogen atoms, said heavy atoms being selected from the group consisting of C, N, O, S, F, Cl, Br, I and any combination thereof wherein the stable substituent is selected from the group consisting of alkyl, alkenyl, alkynyl, phenyl, alkoxy, mercaptoalkyl, acyloxy, amino, halo, $CH_2CN$, CN, $NO_2$ and OH; and n is 0, 1, 2 or 3.

2. The compound of claim 1 wherein $R^1$ is H.
3. The compound of claim 1 wherein $R^1$ and $R^4$ are H and wherein $R^2$ is H or $CH_3$ and wherein $R^3$ is H or $CH_3$.
4. The compound of claim 3 wherein $R^2$ is $CH_3$.
5. The compound of claim 4 wherein $R^3$ is H.
6. The compound of claim 3 wherein $R^2$ is $CH_3$ and $R^3$ is $CH_3$.
7. The compound of claim 3 wherein $R^2$ and $R^3$ are H.
8. The compound of claim 1 having the formula

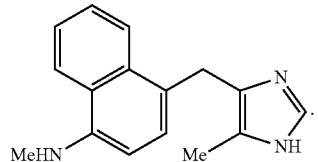

9. The compound of claim 1 having the formula

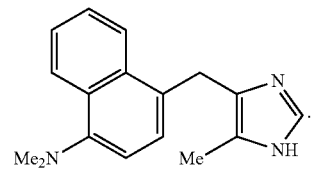

10. The compound of claim 1 having the formula
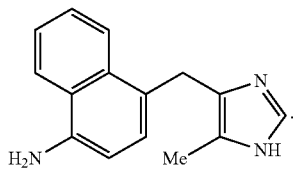
11. The compound of claim 1 having the formula
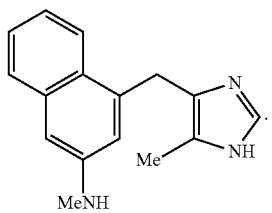
12. The compound of claim 1 having the formula
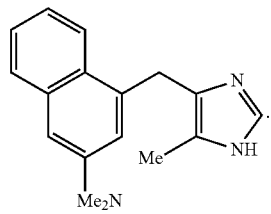
13. The compound of claim 1 having the formula
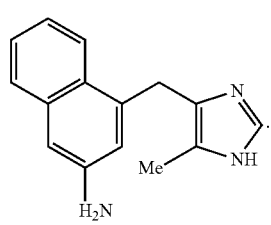
* * * * *